United States Patent [19]

Takahashi et al.

[11] Patent Number: 4,526,893
[45] Date of Patent: Jul. 2, 1985

[54] ISOCARBOSTYRIL DERIVATIVES

[75] Inventors: Toshihiro Takahashi; Noriyoshi Sueda; Masahiro Tsuji, all of Kawagoe; Yoshiyuki Tahara, Tsurugashima; Hiroyasu Koyama, Ageo; Yoshikuni Suzuki, Ohmiya; Masao Nagase, Kawagoe; Toshiji Sugai, Kamifukuoka, all of Japan

[73] Assignee: Nisshin Flour Milling Co., Ltd., Japan

[21] Appl. No.: 562,237

[22] Filed: Dec. 16, 1983

[30] Foreign Application Priority Data

Dec. 24, 1982 [JP] Japan ................. 57-225996

[51] Int. Cl.³ .............. A61K 31/47; C07D 217/24
[52] U.S. Cl. ..................... 514/309; 546/122;
548/473; 564/336; 564/341; 564/347
[58] Field of Search .................. 546/142; 544/258

[56] References Cited

U.S. PATENT DOCUMENTS 4,129,565 12/1978 Fukushima et al. ............... 546/142

FOREIGN PATENT DOCUMENTS 0163367 10/1982 Japan ..................... 546/142
2101990 1/1983 United Kingdom .............. 546/142

OTHER PUBLICATIONS

Fukushima et al., "Chemical Abstracts," vol. 86, 1977, col. 86: 189739n.
Hashimoto et al., "Chemical Abstracts," vol. 98, 1983, col. 98: 83382y.
Shibuya et al., "Chemical Abstracts," vol. 99, 1983, col. 99: 82248t.
Sugai et al., "Chemical Abstracts," vol. 99, 1983, col. 99: 169255s.
Nagatomo et al., "Chemical Abstracts," vol. 100, 1984, col. 100: 96038a.

Primary Examiner—Glennon H. Hollrah
Assistant Examiner—James H. Turnipseed
Attorney, Agent, or Firm—Abelman, Frayne, Rezac & Schwab

[57] ABSTRACT

Compounds of the structure

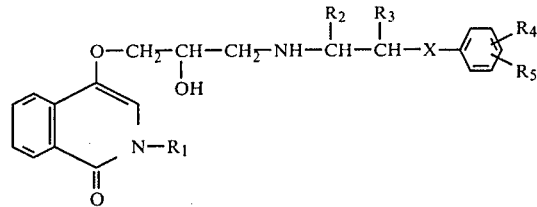

wherein X, $R_1$, $R_2$, $R_3$, $R_4$, and $R_5$ are as herein defined, effective as $\beta$-blockers and hypotensive agents, are described.

4 Claims, No Drawings

ISOCARBOSTYRIL DERIVATIVES

This invention relates to novel isocarbostyril derivatives.

The isocarbostyril derivatives according to this invention have a strong β-blocking effect with a swift blood pressure-reducing activity. They are expected to be used as therapeutic preparations useful for treatment of hypertension and cardiovascular diseases such as angina pectris and arrhythmia, and also glaucoma.

As a β-blocking agent of the similar structure which is useful for treatment of cardiovascular disorders, 4-(3-tert.butylamino-2-hydroxy)propoxy-2-methylisocarbostyril hydrochloride, for example, has hitherto been known (refer to British Pat. No. 1501149). The inventors carried out further investigations in order to obtain compounds which would excel the above-mentioned isocarbostyril derivative in the pharmacological effects and eventually succeeded in obtaining compounds which have strong β-blocking activity and also reduce blood pressure rapidly.

Thus, this invention relates to isocarbostyril derivatives represented by the general formula:

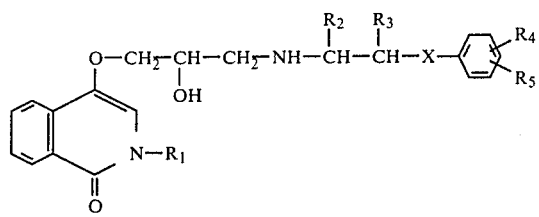

(wherein $R_1$ denotes hydrogen atom or a lower alkyl group; $R_2$ and $R_3$ denote hydrogen atom or a lower alkyl group, respectively; $R_4$ and $R_5$ represent hydrogen atom, halogen atom, lower alkyl group, lower alkoxy group, hydroxy group, amino group, nitro group, lower acylamino group, lower alkylmercapto group, carbamoyl group, sulfamoyl group or hydroxalkyl group, respectively; and X denotes oxygen atom, sulfur atom or imino group), and a process for their preparation, and pharmaceutical compositions thereof for therapy of hypertension and cardiovascular diseases such as angina pectris and also glaucoma.

The isocarbostyril derivatives according to the invention are produced by the methods described below.

Method A

Compound represented by the general formula

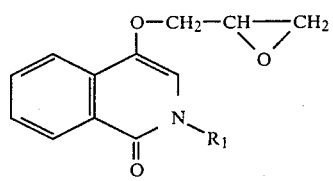

wherein $R_1$ denotes hydrogen atom or lower alkyl group, and compound represented by the general formula

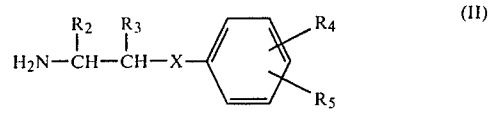

wherein $R_2$ and $R_3$, respectively, denote hydrogen atom or lower alkyl group, $R_4$ and $R_5$, respectively, denote hydrogen atom, halogen atom, lower alkyl group, lower alkoxy group, hydroxy group, amino group, lower acylamino group, nitro group, lower alkylmercapto group, carbamoyl group, sulfamoyl group or hydroxyalkyl group, and X denotes oxygen atom, sulphur atom or imino group, are allowed to react and consequently produce isocarbostyril derivatives represented by the general formula

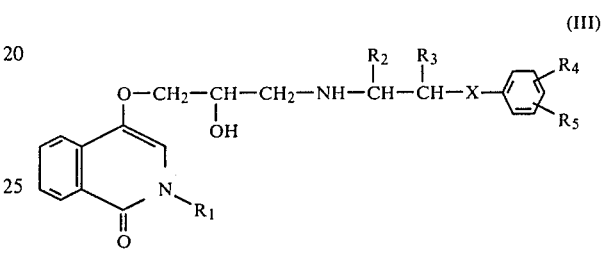

wherein $R_1$, $R_2$, $R_3$, $R_4$ and $R_5$, respectively, denote the same atoms or groups as indicated above. In the compound of general formula (II) wherein $R_4$ and $R_5$ are protected by protective groups, the protective groups can be removed by hydrolysis or hydrogenolysis after the reaction described above. The isocarbostyril derivatives according to the invention can be made into pharmaceutically acceptable salts thereof, when desired, by means of reaction with appropriate inorganic or organic acids.

Method B

Compound represented by the general formula

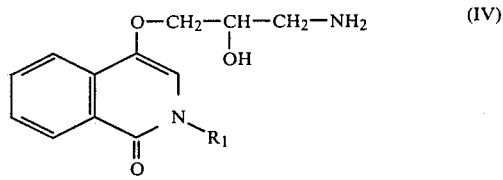

wherein $R_1$ is the same as above, and compound represented by the general formula

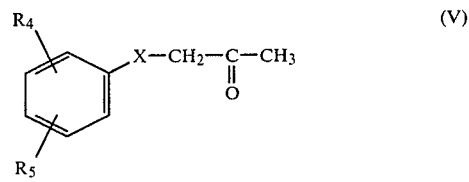

wherein $R_4$, $R_5$ and X are the same as above, are brought to react with each other reductively and consequently give rise to isocarbostyril derivatives represented by the general formula (III). In the compound represented by the general formula (V) wherein $R_4$ and $R_5$ are protected with protective groups, the reaction described above is completed by removing the protective groups by means of hydrolysis or hydrogenolysis. The isocarbostyril derivatives thus obtained can be made, when desired, into pharmaceutically acceptable salts thereof by bringing them to react with appropriate inorganic or organic acids.

Furthermore, the compounds according to this invention may involve optical isomers and structural isomers, as readily understood by experts, because they may posses, in certain instances, 1 to 3 asymmetric carbon atom(s). On such isomers, experts are able to separate them from each other appropriately by known and conventional methods.

Methods for preparation described above will be illustrated in further details.

The reaction of 4-substituted isocarbostyril derivatives represented by the general formula (I) with the amines represented by the general formula (II) in the method A described above is carried out without any solvent at all or in the presence of an organic solvent. As the organic solvents used for the reaction mentioned above, lower alcohols such as methanol and ethanol, ethers such as tetrahydrofuran and dioxane, amides such as N,N-dimethylformamide and others, aromatic hydrocarbons such as benzene and toluene are enumerated. In the reaction mentioned above, amines represented by the general formula (II) are used in the amount of at least equimolar, preferably 3- to 5-fold molar, in proportion to the 4-substituted isocarbostyril derivatives represented by the general formula (I). Reaction temperature is 0° to 200° C., preferably room temperature to 100° C. Approximately 1 to 5 hr. of reaction periods are sufficient.

The reaction of 4-substituted isocarbostyril derivatives represented by the general formula (IV) with the ketones represented by the general formula (V) in the method B is carried out dissolved in organic solvents, for example, alcohols such as methanol and ethanol, ethers such as tetrahydrofuran and dioxane, and aromatic hydrocarbons such as benzene and toluene, as a reductive reaction by means of a reductant or a hydrogenation reaction in the presence of a catalyst. As the reductants used for the reaction described above, lithium aluminum hydride, sodium borohydride and diboran-dimethylamine complex are enumerated. For the catalyst, $Co_2(CO)_8$, palladium-carbon, Raney nickel and platinum can be used. In the method B mentioned above, 4-substituted isocarbostyril derivatives represented by the general formula (IV) and ketones represented by the general formula (V) are used ordinarily in the amount of equimolar proportion. The reductant is used in the amount of at least equimolar, preferably 2- to 3-fold molar proportions. Reaction temperature is 0° to 100° C., preferably around room temperature. Approximately 1 to 20 hr. of reaction periods are sufficient.

Upon the completion of the reaction, reaction mixture is condensed to crystallization under reduced pressure, or the condensate is dissolved in an appropriate solvent, subjected to column chromatography with silica gel or alumina, from which the principal fraction is separated and crystallized to yield the isocarbostyril derivatives represented by the general formula (III).

The isocarbostyril derivatives represented by the general formula (III) shown above according to this invention can be produced as salts of inorganic or organic acids such as hydrochloric, hydrobromic, phosphoric, sulfuric, acetic, citric, maleic, benzoic, oxalic and tartaric in order to prepare pharmacologically acceptable salts thereof, when desired, by dissolving in an organic solvent, adding the corresponding acid in equal amount, and allowing to isolate the salt.

In addition, compounds represented by the general formula (II), which are the starting materials for synthesis of the isocarbostyril derivatives, are produced via the synthetic route described below.

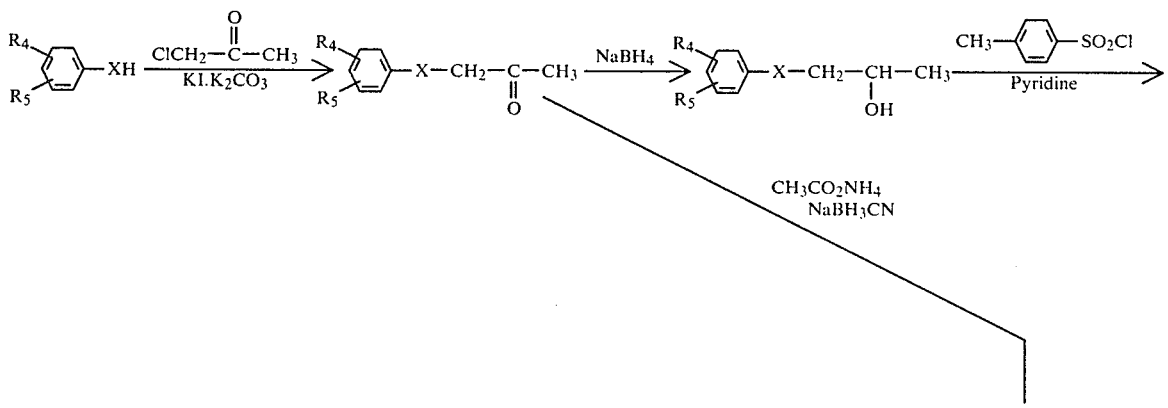

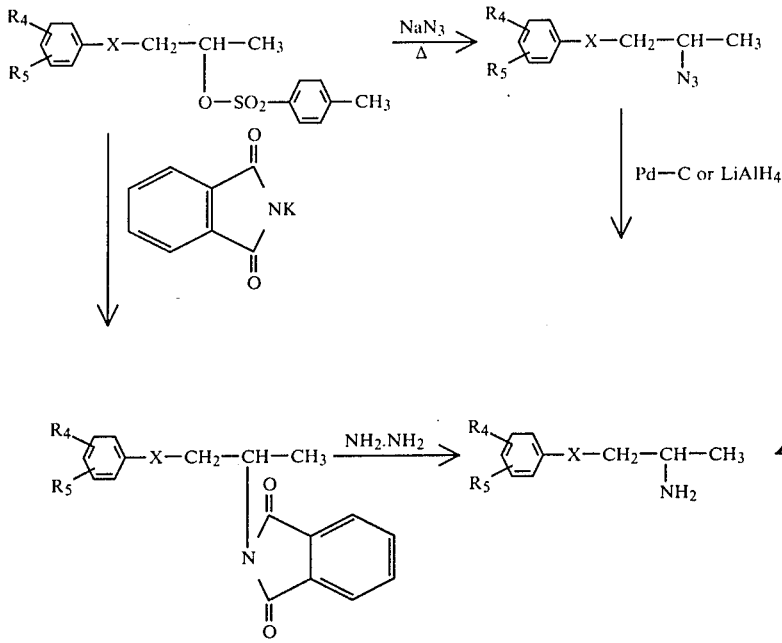

wherein $R_4$, $R_5$ and X denote the same as those described above, respectively.

The isocarbostyril derivatives according to this invention represented by the general formula II exert a strong β-blocking effect and in addition, rapidly exert hypotensive effect via α-blocking and/or not via α-blocking. Due to these pharmacological effects, the said derivatives are useful as antihypertensive agent, antianginal agent, improvement agent for cerebral and peripheral circulations, antiarrhythmic agent, prophylactic agent against myocardial infraction and antiglaucoma agent. Beta-blocking agents hitherto known have to be given to hypertensive patients for some period before desirable effects are obtained. However, the derivatives according to this invention are expected to show rapid antihypertensive effect and thus they are particularly expected to be useful as antihypertensive agents. And further, they show excellent pharmacological properties in that they cause little or no tachycardia compared to labetalol which has hitherto been clinically used as a α- and β-blocking agent, and also are almost free from orthostatic hypotension which constitutes a serious adverse reaction of labetalol. In addition, the acute toxicities of isocarbostyril derivatives according to this invention are remarkably low as shown in Table 1. The said active compounds according to this invention are administered by intravenous injection, subcutaneous injection, intramascular injection, or oral and local (eye drop) application, wherein oral administration is preferable. The doses of the said active compounds for treatment of adult humans lie in a range of 0.1 to 1,000 mg per day, preferably 10 to 500 mg in the oral administration.

TABLE 1

| Acute toxicity of active compounds | | |
|---|---|---|
| | $LD_{50}$ (mg/kg) | |
| Compound | I.V. | P.O. |
| 4-[3-{2-(4-methoxyphenoxy)-1-methyl- | 136.7 | >2,000 |

TABLE 1-continued

| Acute toxicity of active compounds | | |
|---|---|---|
| | $LD_{50}$ (mg/kg) | |
| Compound | I.V. | P.O. |
| ethylamino}-2-hydroxypropoxy]iso-carbostyril hydrochloride | | |
| 4-[3-{2-(4-hydroxyphenoxy)-1-methyl-ethylamino}-2-hydroxypropoxy]iso-carbostyril | 162.8 | >2,000 |
| 4-[3-{2-(4-aminophenoxy)-1-methyl-ethylamino}-2-hydroxypropoxy]iso-carbostyril | 77.4 | >2,000 |
| 4-[3-{2-(2,4-dimethoxyphenoxy)-1-methylethylamino}-2-hydroxy-propoxy]isocarbostyril hydrochloride | 118.5 | >2,000 |

For the oral administration of the said active components according to this invention, tablets, granules and powder preparations are suitable. Granular and powder preparations, in particular, may be formed in capsule preparations to provide unit doses of administration. The solid medicinal preparations for oral administration may contain ordinary diluents such as anhydrous silicic acid, magnesium metaphosphate-aluminate, synthetic aluminium silicate, lactose, sugar (sucrose), corn starch, microcrystalline cellulose, hydroxypropyl-starch or glycine; binders such as gum arabic, gelatin, traganth, hydroxypropyl-cellulose or polyvinyl-pyrrolidone; lubricants such as magnesium stearate, talc or silica; and disintegrators such as potato starch or carboxymethyl-cellulose. Tablets may be coated according to the conventional methods.

Solutions in oil, emulsion and water are suitable for injection. These solvents may be supplemented with additives such as emulsifiers or stabilizers in common use.

Pharmacological effects of the said isocarbostyril derivatives are shown in Table 2 and Table 3 below.

1. β-blocking effect

This was evaluated in terms of the effect antagonizing an increase of beat rate of a right artrium of guinea pig caused by isoproterenol. Efficiency of blocking by the corresponding compound is expressed in $pA_2$ value (see Van Bossum, Arch. int. Pharmacodyn. Ther. 143, 299, 1963).

2. α-blocking effect

This was evaluated in terms of inhibiting contraction of an aorta of rat caused by phenylephrine. Efficency of inhibition by the corresponding compound is expressed by $pA_2$ value.

3. Antihypertensive effect on the spontaneously hypertensive rats

Five spontaneous rats (SHR), showing more than 150 mg of systolic blood pressure were used. After a single oral administration, antihypertensive activity of the corresponding compound was evaluated in terms of a decrease in average blood pressure measured by means of a cannula embedded in the aorta.

4. Influence on the heart rate

This was measured in dogs under unanaesthesized condition after oral administration of the corresponding compound.

Embodiments of this invention in chemical preparation and pharmaceutical manufacturing will be illustrated in the examples below. But this invention shall not be restricted to the said examples.

EXAMPLE 1

A mixture consising of 6.6 g of 4-(2,3-epoxy)propoxy isocarbostyril, 12.8 g of 1-methyl-2-(4-nitrophenoxy)ethylamine and 100 ml of methanol was heated at reflux with stirring for 3 hr. The reaction mixture was concentrated under reduced pressure after completion of the reaction, thereby to yield 19.9 g of reaction product.

The reaction product was eluted with chloroform/methanol on silica gel chromatography and yielded 11.3 g of refined product. The refined product was eluted further with chloroform/methanol on alumina chromatography and yielded 9.5 g of an oily, yellow-colored final product: 4-[3-{1-methyl-2-(4-nitrophenoxy) ethylamino}-2-hydroxypropoxy]isocarbostyril, represented by the formula

TABLE 2

Pharmacological effects of isocarbostyril derivatives

| Compound tested | α-Blocking effect ($pA_2$) | β-Blocking effect ($pA_2$) | Antihypertensive effect | | Influence on heart rate | |
|---|---|---|---|---|---|---|
| | | | Dose (mg/kg) | Decrease in blood pressure (mm Hg) | Dose (mg/kg) | Change |
| 4-[3-{2-(2-methoxyphenoxy)-1-methylethylamino}-2-hydroxypropoxy]isocarbostyril hydrochloride | 7.71 | 7.97 | 30 | 35 | 10 | Slight decrease |
| 4-[3-{2-(2,4-dimethoxyphenoxy)-1-methylethylamino}-2-hydroxypropoxy]isocarbostyril hydrochloride | 7.20 | 8.26 | 30 | 32 | 10 | Slight decrease |
| 4-[3-{2-(4-hydroxyphenoxy)-1-methylethylamino}-2-hydroxypropoxy]isocarbostyril | 6.99 | 8.53 | 30 | 26 | 10 | Slight decrease |
| 4-[3-(1-methyl-2-phenoxy)ethylamino-2-hydroxypropoxy]isocarbostyril hydrochloride | 7.57 | 7.88 | 30 | 15 | 10 | Slight decrease |
| Labetalol (for Comparison) | 7.38 | 7.42 | 30 | 31 | 10 | Increase |

TABLE 3

Pharmacological effects of isocarbostyril derivatives

| Compound tested | Antihypertensive effect | | | Influence on heart rate | |
|---|---|---|---|---|---|
| | β-Blocking effect ($pA_2$) | Dose (mg/kg) | Decrease in blood pressure (mm Hg) | Dose (mg/kg) | Change |
| 4-[3-{2-(4-methoxyphenoxy)-1-methylethylamino}-2-hydroxypropoxy]isocarbostyril hydrochloride | 8.02 | 30 | 21 | 10 | Slight decrease |
| 4-[3-{2-(4-aminophenoxy)-1-methylethylamino}-2-hydroxypropoxy]isocarbostyril hydrochloride | 8.14 | 30 | 31 | 10 | Slight decrease |
| 4-[3-{1-methyl-2-(4-nitrophenoxy)ethylamino}-2-hydroxypropoxy]isocarbostyril hydrochloride | 7.43 | 30 | 17 | 10 | Slight decrease |
| 4-[3-{2-(2-carbamoylphenoxy)-1-methylethylamino}-2-hydroxypropoxy]isocarbostyril | 7.83 | 30 | 10 | 10 | Slight decrease |
| Propranolol (for Comparison) | 7.96 | 30 | 3 | 10 | Decrease |

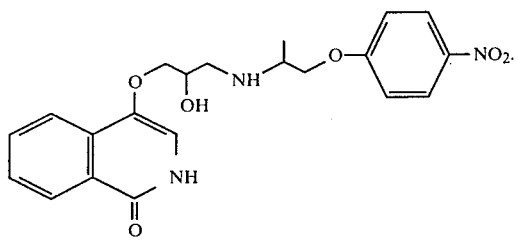

Physical properties of this product are as the following:

N.M.R. (CD$_3$OD+CDCl$_3$) δ; 1.65 (3H d), 6.6–8.4 (9H m).

EXAMPLE 2

9.3 g of 4-[3-{1-methyl-2-(4-nitrophenoxy)ethylamine}-2-hydroxypropoxy]isocarbostyril was dissolved in 250 ml of methanol, added with 500 mg of 10% palladium-carbon, and subjected to catalytic hydrogenation reaction (approximately 1,260 ml of hydrogen was absorbed). The catalyst was filtered off after completion of the reaction, and the remaining fluid (mother liquor) was concentrated and yielded 8.6 g of reaction product. This reaction product was eluted with chloroform/methanol on alumina chromatography, and yielded, after distilling off the solvent, 4.2 g of white crystalline final product: 4-[3-{2-(4-aminophenoxy)-1-methylethylamino}-2-hydroxypropoxy]isocarbostyril represented by the formula

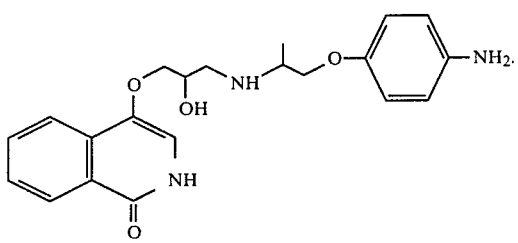

Physical properties of this product are as the following:

m.p. 182.3°–184.4° C.

I.R. (Nujol) (cm$^{-1}$) 3400–2200, 1690, 1630, 1600.

N.M.R. (CDCl$_3$+CD$_3$OD) δ; 1.18 (3H d), 6.62 (5H s), 7.1–8.4 (4H m).

EXAMPLE 3

A mixture consisting of 6 g of 4-(2,3-epoxy)propoxyisocarbostyril, 10.5 g of 2-(4-methoxyphenoxy)-1-methylethylamine and 250 ml of ethanol was stirred at 50° C. for 2.0 hr. After completion of the reaction, reaction fluid was concentrated under reduced pressure and yielded 17.5 g of reaction product. This product was subsequently eluted with chloroform/methanol on silica gel chromatography, pre-treated with triethylamine, and yielded 8.3 g of final product: 4-[3-{2-(4-methoxyphenoxy)-1-methylethylamino}-2-hydroxypropoxy]isocarbostyril, represented by the formula

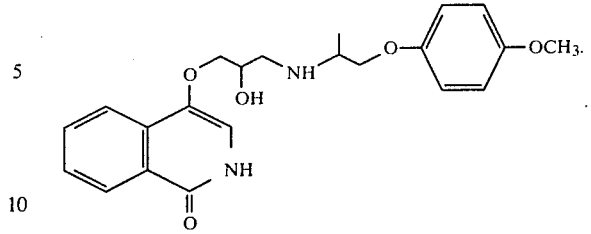

Physical properties of this product are as the following:

I.R. (CHCl$_3$) (cm$^{-1}$) 3400, 3300, 3200, 1640, 1600.

N.M.R. (CDCl$_3$) δ; 1.16 (3H d), 3.63 (3H s), 6.6–8.4 (9H m).

EXAMPLE 4

A mixture consisting of 1.4 g of 4-(2,3-epoxy)propoxyisocarbostyril, 40 ml of concentrated ammonia solution and 200 ml of ethanol was heated at reflux with stirring for 2.5 hr. After completion of the reaction, the reaction fluid was concentrated under reduced pressure, added with 50 ml of isopropyl alcohol, dehydrated by azeotropy, and condensed to dryness. A mixture consisting of 1.4 g of reaction product thus obtained, 1.8 g of 2-carbamoylphenoxyacetone, 500 mg of 10% palladium-charcoal and 3 g of magnesium sulfate was subjected to catalytic hydrogenation reaction at room temperature for 10 hr. (the reaction was incomplete as examined by thin-layer chromatography). Catalyst was filtered off; the filtrate was added with 1.3 g of sodium borohydride, and stirred at room temperature for 20 hr. After distilling off ethanol upon completion of the reaction, reaction product was allowed to separate by adding chloroform/diluted hydrochloric acid solution. The aqueous phase was made alkaline with 10% aqueous solution of sodium hydroxide, and was extracted 7 times with chloroform. The chloroform layer was washed with water and subsequently with saturated saline, dried with anhydrous sodium sulfate, subsequently freed from the solvent by distillation, and finally yielded 2.5 g of reaction product. 2.5 g of this product was eluted with chloroform/methanol on silica gel chromatography pre-treated with triethylamine to yield 1.4 g of final product: 4-[3-{2-(2-carbamoylphenoxy)-1-methylethylamino}-2-hydroxypropy]isocarbostyril, represented by the formula

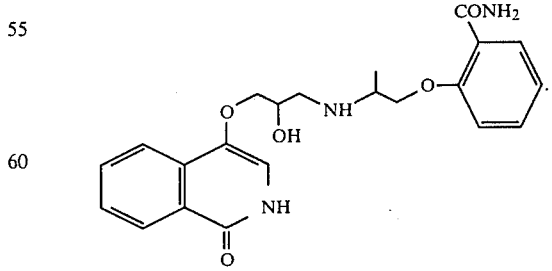

Physical properties of this product are as the following:

N.M.R. (CDCl$_3$) δ; 1.23 (3H d), 6.67 (1H s).

EXAMPLE 5

A mixture consisting of 1.0 g of 4-(2,3-epoxy) propoxyisocarbostyril, 30 ml of concentrated ammonia solution and 150 ml of ethanol was heated at reflux with stirring for 2.5 hr. Reaction fluid was concentrated under reduced pressure upon completion of the reaction, added with about 50 ml of isopropyl alcohol, dehydrated by azeotropy, and was concentrated further to dryness. A mixture consisting of 1.1 g of the reaction product, 1,1 g of 4-acetaminophenoxyacetone, 150 mg of 10% palladium-charcoal and 100 ml of ethanol was subjected to catalytic hydrogenation reaction at room temperature. Catalyst was filtered off after uptake of the calculated amount of hydrogen, and the filtrate was concentrated.

The condensate thus obtained was eluted with chloroform/methanol on alumina chromatography and yielded 0.9 g of an oily substance. This oily substance was dissolved in a mixture of 10 ml of isopropyl alcohol and 10 ml of acetone and was made weakly acidic by adding 1N hydrochloric acid/ether solution. Crystals thus isolated were collected by filtration, washed with acetone, subsequently dried in vacuo and yielded 0.7 g of the final product in white, crystalline form: 4-[3-{2-(4-acetaminophenoxy)-1-methylethylamino}-2-hydroxypropoxy]isocarbostyril hydrochloride, represented by the formula

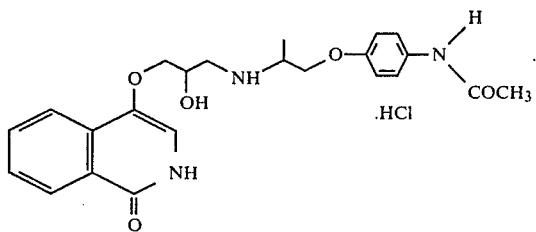

Physical properties of this product are as the following:

N.M.R. (CD$_3$OD) δ free base; 1.21 (3H d), 2.12 (3H s), 6.5–8.45 (9H m).

EXAMPLE 6

A mixture consisting of 2.0 g of 4-(2,3-epoxy)propoxyisocarbostyril, 7.4 g of 2-(4-benzyloxyphenoxy)-1-methylethylamine and 100 ml of ethanol was heated at reflux with stirring for 2 hr. The reaction mixture was concentrated under reduced pressure after completion of the reaction and yielded 9.6 g of reaction product. This reaction product was eluted with chloroform/methanol on silica gel column chromatography and yielded 4.2 g of refined product. This product was eluted with chloroform/methanol on alumina chromatography and yielded 3.8 g of final product in oily form: 4-[3-{2-(4-benzyloxyphenoxy)-1-methylethylamino}-2-hydroxypropoxy]isocarbostyril, represented by the formula

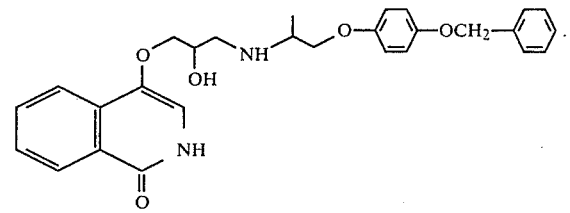

Physical properties of this product are as the following:

I.R. (CHCl$_3$) (cm$^{-1}$) 3400, 3280, 3150, 1645, 1600.

N.M.R. (CDCl$_3$) δ; 1.16 (3H d), 4.94 (2H s), 6.6–6.9 (5H m), 7.2–8.4 (9H m).

EXAMPLE 7

To 0.27 g of 4-(2,3-epoxy)propoxyisocarbostyril and 0.48 g of 2-(4-carbamoylphenoxy)-1-methylethylamine, 6 ml of methanol were added and stirred at 55° to 60° C. for 7 hr. Reaction mixture was concentrated under reduced pressure after completion of the reaction; and the concentrated mass was spotted on two 2 mm-thick plates for thin layer chromatography (Merck Co., 20×20 cm) and subsequently developed with methanol. After recognizing the separation band of the sought compound, the region was scraped off and was extracted with methanol. The extract was allowed to pass through a layer of Hi-Flo super cell, concentrated under reduced pressure and yielded 0.28 g of amorphous solid. This product was dissolved in a small amount of methanol, added with calculated amount of hydrochloric acid solution in methanol, dried up under reduced pressure, and yielded 0.30 g of the final product: 4-[3-{2-(4-carbamoylphenoxy)-1-methylethylamino}-2-hydroxypropoxy]isocarbostyril hydrochloride, represented by the formula

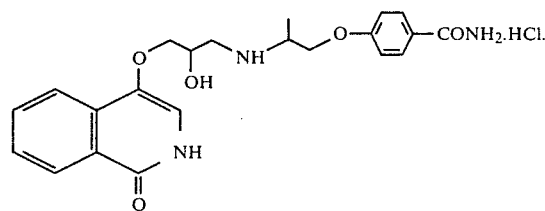

Physical properties of this product are as the following:

I.R. (Nujol) (cm$^{-1}$) 3700–2000, 1700, 1640, 1600.

N.M.R. (DMSO-d$_6$) δ; 1.42 (3H d), 6.8 (1H s), 6.9–8.3 (9H m).

Related compounds were prepared according to procedures similar to that of this example. The compounds obtained are shown in Table 4.

TABLE 4

| Compound | Physical properties |
|---|---|
| 4-[3-{2-(3,4-dimethoxyphenoxy)-1-methylethylamino}-2-hydroxypropoxy]-isocarbostyril | I.R. (CHCl$_3$) (cm$^{-1}$)<br>3400, 3300, 3150, 1640, 1605<br>N.M.R. (CDCl$_3$) δ<br>1.16 (3H c)<br>3.75 (6H s)<br>7.4–8.4 (4H m) |
| 4-[3-{1-methyl-2-(4-methylphenoxy)ethylamino}-2-hydroxypropoxy]isocarbostyril | I.R. (CHCl$_3$)<br>3410, 3300, 3150, 1650, 1610<br>N.M.R. (CDCl$_3$) δ<br>1.18 (3H d)<br>2.26 (3H s)<br>6.6–8.4 (9H m) |
| 4-[3-{1-methyl-2-(4-sulfamoylphenoxy)ethylamino}-2-hydroxypropoxy]-isocarbostyril | I.R. (Nujol) (cm$^{-1}$)<br>3700~200, 1700, 1640, 1600<br>N.M.R. (DMSO-d$_6$) δ<br>1.42 (3H d)<br>6.8 (1H s)<br>6.9–8.3 (9H m) |
| 4-[3-{1-methyl-2-(3-methylphenoxy)ethylamino}-2-hydroxypropoxy]isocarbostyril | I.R. (Nujol) (cm$^{-1}$)<br>3400, 1650, 1610<br>N.M.R. (CDCl$_3$ + CD$_3$OD) δ<br>1.20 (3H d)<br>2.26 (3H s)<br>6.5–8.4 (9H m) |
| 4-[3-{2-(4-methoxyphenoxy)ethylamino}-2-hydroxypropoxy]isocarbostyril | m.p. 215.2~218.1° C. (Hydrochloride)<br>I.R. (Nujol) (cm$^{-1}$)<br>3350, 1650, 1605<br>N.M.R. (DMSO-d$_6$) δ<br>3.66 (3H s)<br>6.70 (1H s)<br>6.79 (4H s) |

TABLE 4-continued

| Compound | Physical properties |
|---|---|
| 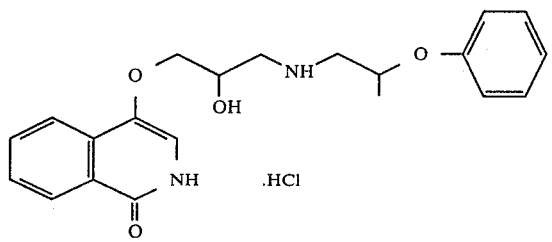<br>4-[3-{2-methyl-2-phenoxyethylamino}-2-hydroxypropoxy]-isocarbostyril hydrochloride | m.p. 194~195.5° C. (Decomp.)<br>I.R. (Nujol)<br>3500~2000, 1690, 1650, 1610<br>N.M.R. (DMSO-$d_6$) δ free base<br>1.3 (3H d)<br>6.7–8.3 (10H m) |
| 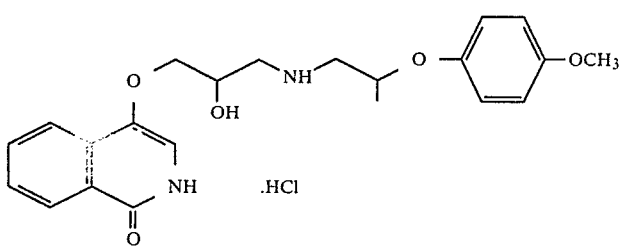<br>4-[3-{2-methyl-2-(4-methoxyphenoxy)ethylamino}-2-hydroxypropoxy]-isocarbostyril hydrochloride | m.p. 188~190° C. (Decomp.)<br>I.R. (Nujol)<br>5500 2000, 1690, 1650, 1610<br>N.M.R. (DMSO-$d_6$) δ free base<br>1.22 (3H d)<br>3.70 (3H s)<br>6.7–8.3 (9H m) |
| 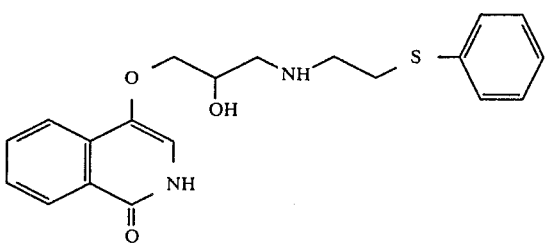<br>4-{3-(2-thiophenoxyethylamino)-2-hydroxypropoxy}isocarbostyril | I.R. (Nujol) (cm$^{-1}$)<br>1680, 1650, 1610<br>N.M.R. (DMSO-$d_6$) δ<br>2.5 4.0 (9H br)<br>6.68 (1H s)<br>7.0–8.2 (10H m) |
| 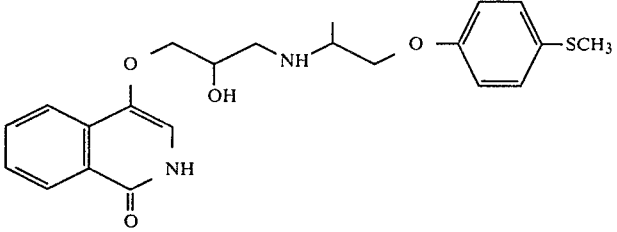<br>4-[3-{1-methyl-2-(4-methylmercaptophenoxy)ethylamino}-2-hydroxy-propoxy)isocarbostyril | m.p. 122° C. (Hydrochloride)<br>N.M.R. (CD$_3$OD) δ Free base<br>1.18 (3H d)<br>2.39 (3H s)<br>6.5–8.5 (9H m) |
| 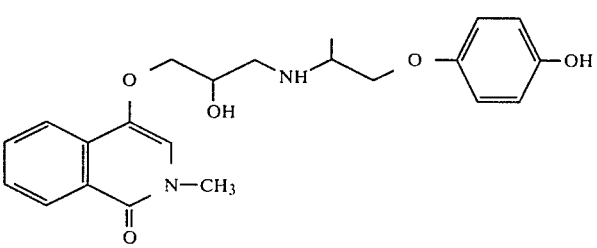<br>4-[3-{2-(4-hydroxyphenoxy)-1-methylethylamino}-2-hydroxypropoxy]-2-methylisocarbostyril | N.M.R. (CDCl$_3$ + CD$_3$OD) δ<br>1.20 (3H d)<br>3.55 (3H s) |

TABLE 4-continued

| Compound | Physical properties |
|---|---|
| <br>4-[3-{1-methyl-2-(4-nitrophenoxy)ethylamino}-2-hydroxypropoxy]-2-methylisocarbostyril | N.M.R. (CDCl$_3$) δ<br>1.23 (3H d)<br>3.45 (3H s)<br>6.43 (1H s)<br>6.5–8.4 (9H m) |
| 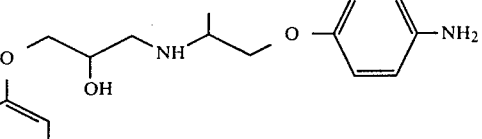<br>4-[3-{2-(4-aminophenoxy)-1-methylethylamino}-2-hydroxypropoxy]-2-methylisocarbostyril | N.M.R. (CD$_3$OD) δ<br>1.18 (3H d)<br>3.53 (3H s) |
| 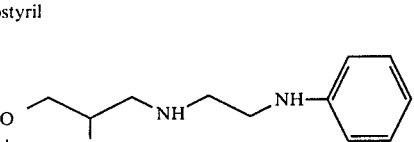<br>4-[3-{2-(N—phenyl)aminoethylamino}-2-hydroxypropoxy]-isocarbostyril | m.p. 224.9° C. (Decomp.) (2HCl crystal)<br>I.R. (Nujol)<br>3325, 3160, 1650, 1610<br>N.M.R. (DMSO-d$_6$) δ<br>2.7–4.2 (9H br)<br>5.33 (1H t)<br>6.5–8.3 (10H m) |
| 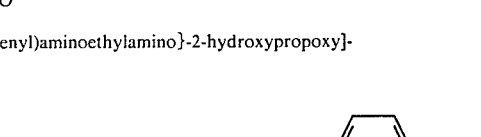<br>4-[3-[1-methyl-2-{4-(2-N,N—dimethylaminoethoxy)phenoxy}ethylamino)-2-hydroxypropoxy]-isocarbostyril | N.M.R. (CDCl$_3$) δ<br>1.16 (3H c)<br>2.30 (6H s)<br>7.3–8.4 (4H) |

EXAMPLE 8

3.6 g of 4-[3-{2-(4-benzyloxyphenoxy)-1-methylethylamino}-2-hydroxypropoxy]isocarbostyril were dissolved in 500 ml of methanol and 3 ml of acetic acid and subjected to catalytic hydrogenation reaction for 10 hr. after adding 420 mg of 10% palladium-charcoal. Catalyst was filtered off after completion of the reaction, and reaction mixture was concentrated. The concentrated mass thus obtained was dissolved in chloroform/methanol mixture (1:1) and washed with 5% aqueous solution of sodium hydrogen carbonate, and the resulting organic phase was concentrated under reduced pressure. The reaction product was dried and yielded 2.9 g of the final product: 4-[3-{2-(4-hydroxyphenoxy)-1-methylethylamino{-2-hydroxy-propoxy]isocarbostyril, represented by the formula

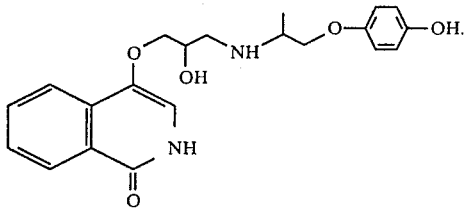

Physical properties of this product are as the following:

m.p. 200.4°–201.5° C.

I.R. (Nujol) (cm$^{-1}$) 3300–3000, 1640, 1605.

N.M.R. (CD$_3$OD+DMSO-d$_6$)δ; 1.10 (3H d), 6.63 (4H s),6.73 (1H s).

EXAMPLE 9

A mixture consisting of 0.7 g of 4-(2,3-epoxy) propoxyisocarbostyril, 4.0 g of 2-(2,4-dimethoxyphenoxy)-1-methylethylamine and 30 ml of ethanol was stirred at room temperature for 1.6 hr. and heated at 50° C. with stirring for additional 2.0 hr. Upon completion of the reaction, reaction mixture was condensed under reduced pressure and yielded 4.9 g of reaction product. This product was eluted with chloroform/methanol on silica gel column chromatography pretreated with triethylamine, and yielded 1.1 g of the final product is an oily form: 4-[3-{2-(2,4-dimethoxyphenoxy)-1-methylethylamino}-2-hydroxyepoxy]isocarbostyril, represented by the formula

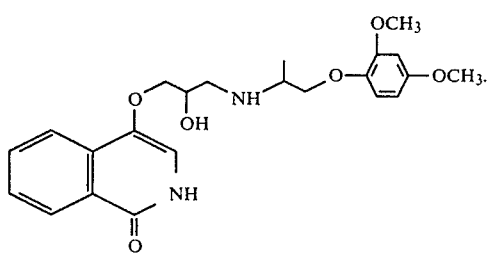

Physical properties of this substance are as the following:

N.M.R. (CDCl$_3$) δ; 1.23 (3H d), 3.71 (3H s), 3.79 (3H s).

EXAMPLE 10

A mixture consisting of 1.0 g of 4-(2,3-epoxy) propoxyisocarbostyril, 5.0 g of 2-(2-methoxyphenoxy)-1-methylethylamine and 50 ml of methanol was heated at reflux with stirring for 2.5 hr. Upon completion of the reaction, reaction mixture was concentrated under reduced pressure and yielded 6.1 g of reaction product. This product was eluted with chloroform/methanol on silica gel chromatography and yielded 1.5 g of refined product. This refined product was eluted with chloroform/methanol on alumina chromatography and yielded 1.1 g of the final product in an oily form: 4-[3-{2-(2-methoxyphenoxy)-1-methylethylamino}-2-hydroxy-propoxy]isocarbostyril, represented by the formula

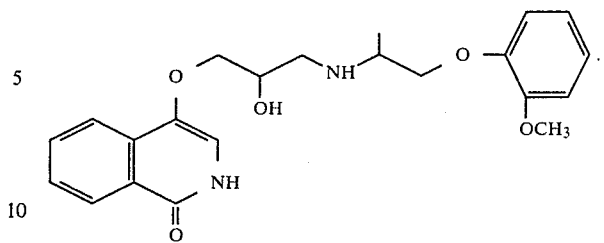

Physical properties of this substance are as the following:

I.R. (Nujol) (cm$^{-1}$) 3150, 1660, 1610.

N.M.R. (DMSO-d$_6$) δ; 1.08 (3H d), 3.72 (3H s), 6.71 (1H s), 6.8–8.4 (8H m).

EXAMPLE 11

A mixture consisting of 2.17 g of 4-(2,3-epoxy) propoxyisocarbostyril, 6.04 g of 1-methyl-2-phenoxyethylamine and 30 ml of ethanol was heated at reflux with stirring for 1.5 hr. Upon completion of the reaction, the reaction mixture was concentrated under reduced pressure, freed from ethanol and eventually isolated crystals. Crystals thus isolated were dissolved in a benzene/isopropylether (1:1) mixture, filtered through a glass filter, and the filtrate was dried in vacuo to yield 3.53 g of reaction product. One gram of this product thus obtained was dissolved in 20 ml of methanol, added with 10 ml of acetone, subsequently added dropwise with saturated hydrogen chloride/ether mixture under stirring and was left standing overnight in a refrigirator. Crystals isolated were filtered off with a glass filter, dried in vacuo and yielded 0.83 g of the final product: 4-[3-(1-methyl-2-phenoxyethyl-amino)-2-hydroxypropoxy]isocarbostyril hydrochloride, represented by the formula

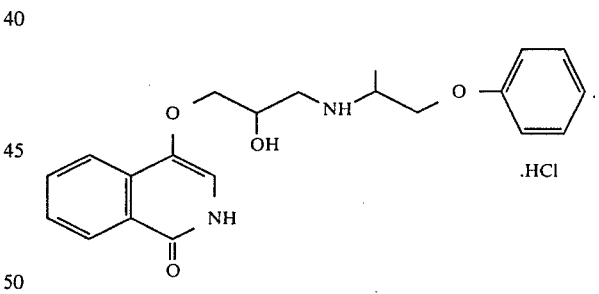

Physical properties of this substance are as the following:

m.p. 182.1°–184.6° C. (Decomp.)

I.R. (Nujol) (cm$^{-1}$) 1690, 1650, 1610, 1600.

N.M.R. (DMSO-d$_6$) δ free base; 1.52 (3H d J=6Hz), 6.7–8.4 (10H m).

EXAMPLE 12

A mixture consisting of 1.5 g of 4-(2,3-epoxy) propoxyisocarbostyril, 9.8 g of 2-(2-isopropylphenoxy)-1-methylethylamine and 50 ml of methanol was heated at reflux with stirring for 2.5 hr. Upon completion of the reaction, reaction mixture was concentrated under reduced pressure and yielded 11.9 g of reaction product. This product was eluted with chloroform/methanol on silica gel column chromatography and yielded 2.6 g of refined product. This refined product was eluted with chloroform/methanol on alumina chromatography and yielded 1.3 g of an oily substance, light yellow in color.

This oily substance was subsequently dissolved in a mixture consisting of 10 ml of isopropyl alcohol and 20 ml of ethyl acetate, made weakly acidic by adding 1N hydrogen chloride/isopropyl alcohol solution. Crystals thus isolated were filtered off, washed with acetone, dried in vacuo, and yielded 1.1 g of the final product in white and powdery crystal form: 4-[3-{2-isopropylphenoxy)-1-methylethylamino}-2-hydroxypropoxy]isocarbostyril hydrochloride, represented by the formula

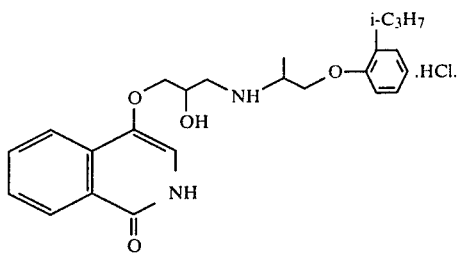

Physical properties of this substance are as the following:

m.p. 123.6°–124.0° C.
I.R. (Nujol) (cm$^{-1}$) 3400–2200, 1650, 1635, 1600.
N.M.R. (CD$_3$OD) δ free base; 1.1–1.3 (9H m), 6.5–8.42 (9H m).

EXAMPLE 13

A mixture consisting of 2.26 g of 4-(2,3-epoxy)propoxy-2-methylisocarbosytril, 6.83 g of 1-methyl-2-phenoxyethylamine and 30 ml of ethanol was heated at reflux with stirring for 1.5 hr. Upon completion of the reaction, ethanol was distilled off under reduced pressure. Reaction product was subjected to silica gel column chromatography. Benzene/methanol (49:1) mixture was employed as the developing solvent. The eluate was examined by thin layer chromatography, and 3.01 g of refined product was obtained from the principal fraction. The refined product was dissolved in 60 ml of acetone and added dropwise with saturated hydrogen chloride/ethanol solution. Crystals isolated were filtered off with a glass filter, washed with acetone, subsequently dried in vacuo, and yielded 2.57 g of the final product in white crystal form: 4-[3-(1-methyl-2-phenoxyethylamino-2-hydroxypropoxy]-2-methyl-isocarbosytril hydrochloride, represented by the formula

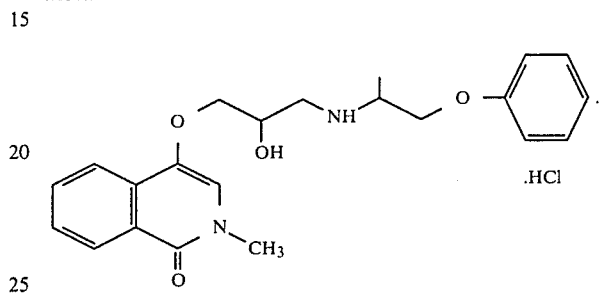

Physical properties of this substance are as the following:

m.p. 175°–205° C. (Decomp.)
I.R. (Nujol) (cm$^{-1}$) 2350–2800, 1660, 1630, 1600, 1580.
N.M.R. (DMSO-d$_6$) δ free base; 1.47 (3H d J=6Hz), 3.50 (3H s), 6.8–8.4 (10H m).

Related compounds shown in the following Table 5 were prepared in the same way as that of the example described above.

TABLE 5

| Compound | Physical properties |
|---|---|
| 4-[3-{1-methyl-2-(2-methylphenoxy)ethylamino}-2-hydroxypropoxy]isocarbostyril | I.R. (CHCl$_3$) (cm$^{-1}$) 3400, 3300, 3150, 1650, 1605<br>N.M.R. (CDCl$_3$) δ<br>1.20 (3H d)<br>2.16 (3H s)<br>6.6–8.4 (9H m) |
| 4-[3-{2-(2,4-dimethylphenoxy)-1-methylethylamino}-2-hydroxypropoxy]isocarbostyril | I.R. (CHCl$_3$) (cm$^{-1}$) 3400, 3150, 1650, 1605<br>N.M.R. (CDCl$_3$ + CD$_3$OD) δ<br>1.21 (3H d)<br>2.13 (3H s)<br>2.22 (3H s)<br>6.5–8.4 (8H m) |

TABLE 5-continued

| Compound | Physical properties |
|---|---|
| 4-[3-{2-(2,6-dimethoxyphenoxy)-1-methylethylamino}-2-hydroxy-propoxy]isocarbostyril | I.R. (CHCl$_3$) (cm$^{-1}$)<br>3420, 3300, 3150, 1650, 1610<br>N.M.R. (CDCl$_3$) δ<br>1.10 (3H d)<br>3.78 (6H s)<br>6.4–8.4 (8H m) |
| 4-[3-{2-(2-methoxyphenoxy)-1-methylethylamino}-2-hydroxypropoxy]-2-methylisocarbostyril | I.R. (Nujol) (cm$^{-1}$)<br>1640, 1630, 1605<br>N.M.R. (CDCl$_3$) δ<br>1.17 (3H d)<br>3.52 (3H s)<br>3.77 (3H s)<br>6.4–8.4 (8H m) |
| 4-[3-{2-(2-carbamoylphenoxy)-1-methylethylamino}-2-hydroxypropoxy]-2-methylisocarbostyril | N.M.R. (CD$_3$OD) δ<br>1.25 (3H s)<br>3.55 (3H s)<br>6.4–8.4 (8H m) |
| 4-[3-(1-methyl-2-phenoxyethylamino)-2-hydroxypropoxy]-2-methylisocarbostyril | N.M.R. (CDCl$_3$) δ<br>1.16 (3H d)<br>3.46 (3H s)<br>6.47–8.4 (10H m) |
| 4-[3-{1-ethyl-2-(methoxyphenoxy)ethylamino}-2-hydroxypropoxy]isocarbostyril | N.M.R. (CDCl$_3$) δ<br>0.97 (3H t)<br>1.54 (2H m)<br>3.75 (3H s)<br>6.70 (1H s)<br>6.5–8.5 (8H m) |

TABLE 5-continued

| Compound | Physical properties |
|---|---|
| [structure]<br>4-{3-(2-phenoxyethylamino)-2-hydroxypropoxy}isocarbostyril | m.p. 220.5–221.7° C. (Hydrochloride)<br>I.R. (Nujol) Hydrochloride (cm$^{-1}$)<br>3400–2000, 1625, 1603, 1595<br>N.M.R. (CD$_3$OD) δ<br>6.6–8.5 (10H m) |
| [structure]<br>4-[3-{2-(2-methoxyphenoxy)ethylamino}-2-hydroxypropoxy]isocarbostyril | m.p. 107.7° C. (Hydrochloride)<br>I.R. (Nujol) (cm$^{-1}$)<br>3300–3500, 1650, 1605<br>N.M.R. (DMSO-d$_6$) δ<br>3.70 (3H s)<br>6.73 (1H s)<br>6.86 (4H s)<br>6.8–8.5 (5H m) |
| [structure]<br>4-[3-{2-(2-chlorophenoxy)ethylamino}-2-hydroxypropoxy]isocarbostyril | I.R. (Nujol) (cm$^{-1}$)<br>3270, 1675, 1650, 1610<br>N.M.R. (DMSO-d$_6$) δ<br>2.70 (4H)<br>3.8–4.2 (5H br)<br>6.70 (1H s)<br>6.5–8.5 (9H m) |
| [structure]<br>4-[3-(1,2-dimethyl-2-phenoxyethylamino)-2-hydroxypropoxy]isocarbostyril | m.p. 127° C. (Decomp.) (Hydrochloride)<br>I.R. (Nujol) Hydrochloride (cm$^{-1}$)<br>3400–2200, 1635, 1590<br>N.M.R. (CD$_3$OD) δ<br>1.0–1.3 (6H m)<br>6.6–8.6 (10H m) |

EXAMPLE A

Tablets

| | |
|---|---|
| 4-[3-{2-(2,4-dimethoxyphenoxy)-1-methylethylamino}-2-hydroxypropoxy]isocarbostyril hydrochloride | 30 mg |
| Calcium hydrogen phosphate | 97 mg |
| Crystalline cellulose | 15 mg |
| Corn starch | 7 mg |
| Magnesium stearate | 1 mg |
| | 150 mg |

The ingredients are mixed to make uniform powder ready for making tablets. Tablets are molded by rotary tablet machine to make the product apiece 7 mm in diameter and 150 mg in weight. Hardness of these tablets is 5 to 6 kg, and disintegration time is 0.5 to 1.0 min.

EXAMPLE B

Fine granules

| | | |
|---|---|---|
| 4-[3-{2-(4-aminophenoxy)-1-methylethylamino}-2-hydroxypropoxy]isocarbostyril | 30 mg | ⎫ |
| Lactose | 300 mg | ⎬ A |
| Corn starch | 110 mg | |
| Crystalline cellulose | 50 mg | ⎭ |

-continued

| Hydroxypropyl cellulose | 10 mg | B |
| Ethanol | 90 mg | |

Components of group A are mixed together into homogeneous material, to which solution of B is added and mixed. Granules made by extrusion grain machine and dried in a box-type drying oven. Granules thus dried up are separated by means of 32- and 150-mesh sieves to give the final medicinal composition. These granules are divided into 500 mg per day packs as the final product.

EXAMPLE C

Hard capsules

| 4-[3-{2-(2-methoxyphenoxy)-1-methylethylamino}-2-hydroxypropoxy]isocarbostyril hydrochloride | 30 mg |
| Spray-dried lactose | 158 mg |
| Crystalline cellulose | 10 mg |
| Magnesium stearate | 2 mg |
| | 200 mg |

The components are mixed together. The mixture, 200 mg apiece, is filled into No. 3 lock capsules to make the final medicinal product.

EXAMPLE D

Parenteral solution

| 4-[3-{2-methyl-2-phenoxyethylamino}-2-hydroxypropoxy]-isocarbostyril hydrochloride | 5 mg |
| Sodium chloride | 10 mg |
| Distilled water added to make up | 1.0 ml |

Preparation of Starting Materials

Preparation 1

A mixture consisting of 35 g of 4-nitrophenol, 35 g of chloroacetone, 35 g of potassium carbonate, 1 g of potassium iodide and 500 ml of acetone was heated at reflux with stirring for 3 hr. Reaction mixture was concentrated underd reduced pressure; the concentrate was extracted with ethyl acetate; the ethyl acetate layer was washed consecutively with 5% aqueous solution of sodium hydroxide, water and saturated saline; and dried with anhydrous sodium sulfate. The solvent was distilled off under reduced pressure; the residue was dissolved in 300 ml of ethanol, added with 100 ml of n-hexane; and subsequently left standing overnight at room temperature. Yellow crystals thus isolated were filtered off, dried and yielded 43.5 g of 4-nitrophenoxyacetone.

43.5 g of 4-nitrophenoxyacetone crystals were dissolved in 300 ml of ethanol, added portionwise with small amount of sodium boron hydride up to 4.1 g with stirring at room temperature, and stirred thereafter at room temperature for 2 hr. After adding 10 ml of saturated aqueous solution of ammonium chloride under an ice-cold condition in order to decompose the residual sodium borohydride, extraction was carried out with ethyl acetate. The ethyl acetate layer was washed consecutively with water, 3% hydrochloric acid, 5% aqueous solution of sodium hydrogen carbonate, water and saturated saline and subsequently dried with anhydrous sodium sulfate. The solvent was concentrated under reduced pressure and yielded 46.3 g of 2-(4-nitrophenoxy)-1-methylethanol.

46.3 g of 2-(4-nitrophenoxy)-1-methylethanol was dissolved in 150 ml of pyridine, added with 49 g of p-toluene sulfonyl chloride and left standing overnight at room temperature. The reaction mixture was extracted with ethyl acetate; the ethyl acetate layer was washed consecutively with water, 3% hydrochloric acid, 5% aqueous solution of sodium hydrogen carbonate, water and saturated saline; and subsequently dried with anhydrous sodium sulfate. The solvent was thereafter distilled off under reduced pressure and yielded 77.0 g of 2-(4-nitrophenoxy)-1-methylethyl-p-toluenesulfonate.

A mixture consisting of 77 g of 2-(4-nitrophenoxy)-1-methylethyl-p-toluenesulfonate, 45 g of potassium salt of phthalimide and N,N-dimethylformamide was heated at 110° C. for 3 hr. with stirring. The reaction mixture was extracted with ethyl acetate; the extract was washed consecutively with water and saturated saline, and dried with anhydrous sodium sulfate. The solvent was thereafter distilled off under reduced pressure; the residue was dissolved in ethanol and left standing overnight in refrigirator. Crystals thus isolated were filtered off, dried, and yielded 38.5 g of N-{2-(4-nitrophenoxy)-1-methylethyl}phthalimide in crystalline form.

A mixture consisting of 38.5 g of N-{2-(4-nitrophenoxy)-4-methylethyl}phthalimide crystals, 20 ml of hydrazine hydride and 500 mp of ethanol was heated at reflux with stirring for 3 hr. Upon completion of the reaction, benzene was added for extraction; the extract was washed several times with 20% aqueous solution of sodium hydroxide and thereafter with water and saturated saline, and subsequently dried with anhydrous sodium sulfate. The solvent was condensed after drying under reduced pressure and yielded 12.8 g of 2-(4-nitrophenoxy)-1-methylethylamine in yellow, oily form.

Physical properties of this substance are as the following:

N.M.R. (CDCl$_3$) δ: 1.26 (3H d), 1.60 (2H s, disappeared in D$_2$O), 3.35 (1H q) 3.6–4.1 (2H m), 6.93 (2H d), 8.13 (2H d).

Preparation 2

A mixture consisting of 24.0 g of o-isopropylphenol, 17.0 g of chloroacetone, 30 g of potassium carbonate, 1.0 g of potassium iodide and 150 ml of acetone was heated at reflux with stirring for 6 hr. The reaction mixture was concentrated under reduced pressure; the condensate was extracted with ethyl acetate; the ethyl acetate layer was washed consecutively with 5% aqueous solution of sodium hydroxide, water and saturated saline, and thereafter dried with anhydrous sodium sulfate. The solvent was thereafter distilled off under reduced pressure and yielded 38 g of 2-isopropylphenoxyacetone.

The crude product of 2-isopropylphenoxyacetone, obtained as above, amounting to 38 g was dissolved in 150 ml of ethanol, added portionwise with small amount of sodium borohydride at room temperature wih stirring and stirred for additional 2 hr at room temperature. Thereafter, the reaction mixture was added with 10 ml of saturated aqueous solution of ammonium chloride under an ice-cold condition in order to decompose the residual sodium borohydride, and subsequently extracted with ethyl acetate. The ethyl acetate layer was washed consecutively with water, 3% hydrochloric acid, 5% aqueous solution of sodium hydrogen carbonate, water and saturated saline, and subsequently dried with anhydrous sodium sulfate. The solvent was thereafter distilled off under reduced pressure and yielded 33.1 g of 2-(2-isopropylphenoxy)-1-methylethanol.

The crude product of 2-(2-isopropylphenoxy)-1-methylethanol obtained as above amounting to 33.1 g was dissolved in 100 ml of pyridine, added with 34 g of p-toluenesulfonyl chloride, and left standing overnight at room temperature. The reaction mixture was extracted with ethyl acetate; the ethyl acetate layer was washed consecutively with water, 3% hydrochloric acid, 5% sodium hydrogen carbonate, water and saturated saline; and dried with anhydrous sodium sulfate. The solvent was subsequently distilled off under reduced pressure and yielded 45.0 g of condensate. This condensate was eluted with hexane/benzene on alumina column chromatography and yielded 32.6 of 2-(2-isopropylphenoxy)-1-methylethyl-p-toluenesulfonate.

A mixture consisting of 21.0 g of 2-(2-isopropylphenoxy)-1-methylethyl-p-toluenesulfonate, 3.9 g of sodium azide and N,N-dimethylformamide was heated at 70° to 75° C. for 5 hr. with stirring. Upon completion of the reaction, the mixture was extracted with ethyl acetate; the extract was washed consecutively with water and saturated saline; and subsequently dried with anhydrous sodium sulfate. The solvent was thereafter distilled off under reduced pressure and yielded 21.6 g of 2-(2-isopropylphenoxy)-1-methylethylazide.

12.3 g of 2-(2-isopropylphenoxy)-1-methylethylazide was dissolved in 150 ml of ether and added portionwise with small amount of lithium aluminium hydride up to 18 g and stirred at room temperature for 2.5 hr. Then 1.8 ml of water, 1.8 ml oif 15% aqueous solution of sodium hydroxide and 5.4 ml of water were added one after another in order to decompose the residual lithium aluminium hydride. Crystals thus isolated were filtered off and washsed with ether; the ether layer was washed consecutively with water and saturated saline and dried with anhydrous sodium sulfate. The solvent was distilled off under reduced pressure and yielded 9.8 g of 2-(2-isopropylphenoxy)-1-methylethylamine. Physical properties of this substance are as the following:

N.M.R. 1.05–1.30 (9H m), 2.75 (2H s, disappeared in $D_2O$), 3.1–4.00 (4H m), 6.65–7.2 (4H m).

Related compounds shown in Table 6 below were produced in the same way.

TABLE 6

$$\underset{R_2}{\overset{R_1}{\underset{|}{\text{NH}_2}}}\overset{|}{\underset{|}{\text{C}}}-\text{X}-\text{A}$$

| $R_1$ | $R_2$ | X | A | IR (cm$^{-1}$) | Physical properties N.M.R. ($\delta$) |
|---|---|---|---|---|---|
| CH$_3$ | H | O | —C$_6$H$_4$—CH$_2$OH (para) | | 1.13 (3H, d), 2.37 (3H, b) 3.25 (1H, m), 3.73 (2H, m) 4.50 (2H, s), 6.75 (2H, d) 7.18 (2H, d), (CDCl$_3$) |
| CH$_3$ | H | O | —C$_6$H$_4$—CONH$_2$ (para) | 3400, 3340, 3300 3180, 1650, 1610 (Nujol) | 1.05 (3H, d), 3.15 (3H, b) 3.76 (2H, d), 6.96 (2H, d) 7.12 (2H, b), 7.80 (2H, d) (DMSO-d$_6$) |
| CH$_3$ | H | O | —C$_6$H$_4$—SO$_2$NH$_2$ (para) | 3360, 3300, 3100 1600, 1580 (Nujol) | 1.06 (3H, d), 3.15 (1H, m) 3.80 (2H, d), 4.53 (4H, b) 7.02 (2H, d), 7.70 (2H, d) (DMSO-d$_6$) |
| H | CH$_3$ | O | —C$_6$H$_4$—OCH$_3$ (para) | 3360, 3300, 1590 (Neat) | 1.23 (3H, d), 1.30 (2H, b) 2.83 (2H, d), 3.72 (3H, s) 4.20 (1H, m), 6.80 (4H, s) (CDCl$_3$) |
| CH$_3$ | H | O | 2-CH$_3$, 4-OCH$_3$-C$_6$H$_3$— | | 1.24 (3H, d), 2.30 (3H, s) 3.80 (3H, s), 3.9 (3H, m) (CDCl$_3$) |
| CH$_3$ | H | O | 2-OCH$_3$, 4-OCH$_3$-C$_6$H$_3$— | | 1.22 (3H, d), 3.72 (3H, s) 3.80 (3H, s), 3.8 (3H, m) (CDCl$_3$) |
| CH$_3$ | H | O | —C$_6$H$_4$—F (para) | | 1.25 (3H, d), 3.6 (3H, m) (CDCl$_3$) |

TABLE 6-continued

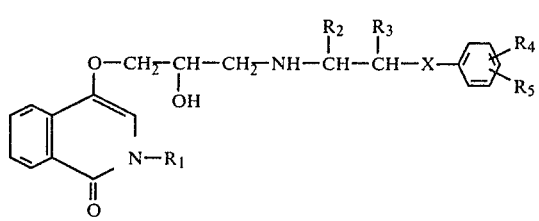

| $R_1$ | $R_2$ | $X$ | A | IR (cm$^{-1}$) | Physical properties N.M.R. ($\delta$) |
|---|---|---|---|---|---|
| CH$_3$ | H | O | [4-benzyloxyphenyl] | | 1.10 (3H, d) 1.43 (2H, s Disappeared in D$_2$) 3.03 3.96 (3H, m) 4.92 (2H, s) 6.72 (4H, s) 7.30 (5H, br) (CDCl$_3$) |

What we claim is:

1. Isocarbostyril derivative represented by the general formula

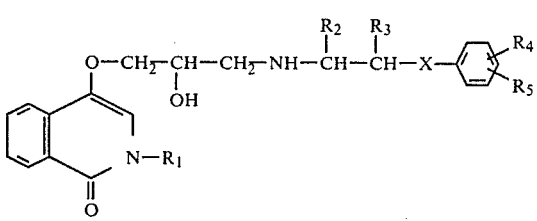

wherein $R_1$ denotes hydrogen atom or a lower alkyl group, $R_2$ and $R_3$ denote hydrogen atom or a lower alkyl group, respectively, $R_4$ and $R_5$ denote hydrogen atom, halogen atom, a lower alkyl group, lower alkoxy group, hydroxy group, amino group, lower acylamino group, nitro group, lower alkylmercapto group, carbamoyl group, sulfamoyl group or hydroxyalkyl group, respectively, and X denotes oxygen atom, sulfur atom or imino group.

2. 4-[3-{2-(2,4-dimethoxyphenoxy)-1-methylethylamino}-2-hydroxypropoxy]isocarbostyril.

3. 4[3-{2-(2-methoxyphenoxy)-1-methylethylamino}-2-hydroxypropoxy]isobcarbostyril.

4. A pharmaceutical composition which comprises as an active ingredient a compound of the general formula wherein $R_1$ denotes hydrogen atom or a lower alkyl group, $R_2$ and $R_3$ denote hydrogen atom or a lower alkyl group, respectively, $R_4$ and $R_5$ denote hydrogen atom, halogen atom, a lower alkyl group, lower alkoxy group, hydroxy group, amino group, lower acylamino group, nitro group, lower alkylmercapto group, carbamoyl group, sulfamoyl group or hydroxyalkyl group, respectively, and X denotes oxygen atom, sulfur atom or imino group.

* * * * *